(12) United States Patent
Van Herk et al.

(10) Patent No.: US 8,996,100 B2
(45) Date of Patent: Mar. 31, 2015

(54) MONITORING SYSTEM COMPRISING ELECTRODES WITH PROJECTIONS

(75) Inventors: Johannes Johanna Van Herk, Eindhoven (NL); Markus Cornelis Jakobus Lazeroms, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 2872 days.

(21) Appl. No.: 10/509,239

(22) PCT Filed: Mar. 6, 2003

(86) PCT No.: PCT/IB03/00851
§ 371 (c)(1),
(2), (4) Date: Sep. 24, 2004

(87) PCT Pub. No.: WO03/082104
PCT Pub. Date: Oct. 9, 2003

(65) Prior Publication Data
US 2005/0107713 A1      May 19, 2005

(30) Foreign Application Priority Data
Mar. 29, 2002  (EP) .................................... 02076230

(51) Int. Cl.
*A61N 1/05*       (2006.01)
*A61B 5/00*       (2006.01)
*A61B 5/0408*     (2006.01)

(52) U.S. Cl.
CPC ........... *A61B 5/6804* (2013.01); *A61B 5/04085* (2013.01)

USPC ............... 600/509; 600/508; 607/1; 607/2; 607/3; 607/4; 607/5; 607/6; 607/53; 607/54; 607/115; 607/152; 607/153

(58) Field of Classification Search
USPC ............. 607/1–6, 53–54, 115–116, 152–153; 600/508–509
See application file for complete search history.

(56) References Cited

U.S. PATENT DOCUMENTS

| 3,998,213 | A | | 12/1976 | Price |
| 4,082,087 | A | | 4/1978 | Howson |
| 4,646,747 | A | * | 3/1987 | Lundback ..................... 600/387 |
| 4,669,479 | A | * | 6/1987 | Dunseath, Jr. ................ 600/391 |
| 4,729,377 | A | * | 3/1988 | Granek et al. ................ 600/393 |
| 4,751,928 | A | | 6/1988 | Hallon et al. |
| 4,969,468 | A | * | 11/1990 | Byers et al. ................... 600/373 |
| 6,004,312 | A | | 12/1999 | Finneran et al. |
| 6,148,233 | A | * | 11/2000 | Owen et al. ....................... 607/5 |
| 2002/0082668 | A1 | * | 6/2002 | Ingman ........................... 607/98 |
| 2003/0114906 | A1 | * | 6/2003 | Booker et al. ................ 607/122 |

FOREIGN PATENT DOCUMENTS

| JP | 58152940 | 9/1983 |
| JP | 59022113 | 2/1984 |

(Continued)

*Primary Examiner* — Rex R Holmes

(57) ABSTRACT

An electrode structure for use with a monitoring system. A thin flexible body of an electrode material comprising conductive rubber is provided with projections extending externally to a working surface. According to this construction of the working surface of the electrode only the projections make a contact to the recipient's skin. When the projections are provided with a small cross-section, the constant electrode-skin contact is ensured due to the resiliency of the electrode material.

5 Claims, 2 Drawing Sheets

(56) References Cited

FOREIGN PATENT DOCUMENTS

Figure 1:
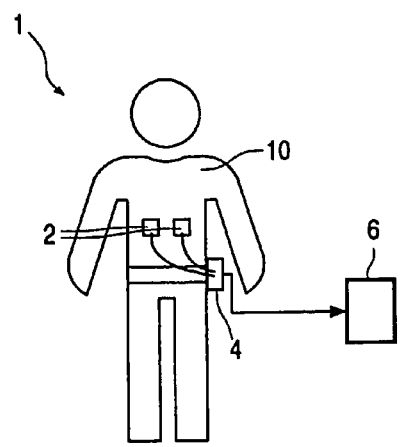

| JP | 63046134 | 2/1988 |
| JP | 2131406 | 11/1990 |
| JP | 2299668 | 12/1990 |
| JP | 10165386 | 6/1998 |

* cited by examiner

MONITORING SYSTEM COMPRISING ELECTRODES WITH PROJECTIONS

The invention relates to a monitoring system for monitoring of a physiological activity of a recipient, comprising a set of electrodes having a working surface to be brought into a contact with the recipient's skin.

The invention further relates to electrodes for use in the monitoring system according to the invention.

A monitoring system is known from U.S. Pat. No. 4,082, 087. Such a monitoring system is arranged for monitoring a heart rate. The electrodes utilized in the known system are arranged in an electrode assembly to be positioned on the skin of a patient. The electrode assembly comprises an electrically non-conductive envelope which houses a number of electrodes. In the known system in order to improve the electrical contact between the electrodes and the skin of the patient a conductive jelly is applied between a working surface of the electrode and the corresponding skin area of the patient. Further, a number of projections is provided on the surface of the non-conductive envelope in the areas between the electrodes of the assembly. This technical measure is used to localize the conductive jelly on the working surface of the electrodes better, thus preventing a leakage of the jelly from areas above the electrodes, causing undesirable electrical interconnections of the electrodes.

The known monitoring system has a disadvantage that for a good functioning of the assembly extra technical measures must be undertaken to prevent leakage of the conductive jelly. Next to this, the known monitoring system is less reliable due to the fact that the electrode assembly in the operational condition is movable with respect to the skin of the patient.

It is an object of the invention to provide a reliable monitoring system, in which the electrodes have a substantially constant contact with the patient's skin.

The monitoring system according to the invention is characterized in that each electrode comprises a body of an electrically conductive elastic material with the working surface exhibiting projections so as to enable a substantially constant position of the contact with the recipient's skin. The technical measure according to the invention has the advantage that due to the fact that the electrodes are manufactured from an elastic material they can be directly applied to the patient's skin without any use of a conductive jelly. Such electrodes are often referred to as dry electrodes. Next to this, the projections arranged on the working surface of the electrode due to the use of an elastic material exhibit a certain degree of resiliency in two directions, enabling a better mechanical contact with the skin. Even in situations when the body of the electrode is slightly moving the tips of the projections stay on the same place due to the resilience of the electrode material. Also, the skin irritation of the patient is reduced due to the fact that only projections, having preferably a small cross-section are in a direct contact with the skin.

An embodiment of the monitoring system according to the invention is characterized in that the projections are arranged in a substantially uniform distributed pattern over the working surface with spacings between them. According to this technical measure the electrode body is provided with a better and uniformly distributed mechanical support.

A further embodiments of the monitoring system according to the invention is characterized in that the projections comprise metal particles. Due to this technical measure a better electric conductivity of the electrode material is ensured. In general, any non-toxic metal is appropriate for this purpose. Preferably Ag is used, as it has been found that Ag makes a good contact with the skin. Next to this, it is also possible to provide the surface of the projection with a metal coating.

A still further embodiment of the monitoring system is characterized in that the electrode body is sandwiched between two layers of an insulating material, tips of the projections being arranged to extend beyond a body of an isolating layer. According to this technical measure the resulting electrode structure is protected against mechanical disruptions adding to the durability of the system as a whole.

A still further embodiment of the monitoring system according to the invention is characterized in that said system is a cardiac arrest monitoring system. Although a monitoring system of the type presented above can be utilized for a wide variety of applications, it is particularly suited for applications in the cardiac monitoring due to the fact that in this application the patient is required to wear the monitoring system continuously. This requirement is easily met only when the electrodes do not impose discomfort to the patient, particularly skin irritation. The monitoring system according to the invention provides suitable electrodes for continuous monitoring purposes.

A still further embodiment of the monitoring system according to the invention is characterized in that the electrodes are mounted on a fabric-based elastic belt of a wearable garment. The fact that the necessary electrodes are integrated in the belt of the garment contributes to the user-friendliness of such a monitoring system. For a reliable operation the dry electrodes must be attached to the skin with some pressure. A higher pressure reduces movement artifacts and decreases the impedance between the electrode and the skin, both features improving the reliability of the system. However, the pressure is generated by the elasticity of the belt. A shorter belt length with respect to the body's circumference increases the applied pressure but leads to a user's discomfort. Electrodes with projections generate a higher pressure between the projections and the skin without reducing the length of the belt thus not altering a user's comfort.

Furtheron such a system can be made washable which further contributes to the comfort of the patient. Due to the fact that the electrodes are integrated with the elastic band, a rigid electrode mounting is enabled, providing a fixed position of the electrodes with respect to the patient's skin, thus further minimizing the motion artifacts of the measurements performed by the monitoring system.

These and other aspects of the invention will be explained with reference to the figures.

FIG. 1 presents a schematic view of an embodiment of the monitoring system.

FIG. 2 presents a schematic view of an embodiment of a structure of the working surface of the electrode to be used in the monitoring system.

Figure 3:
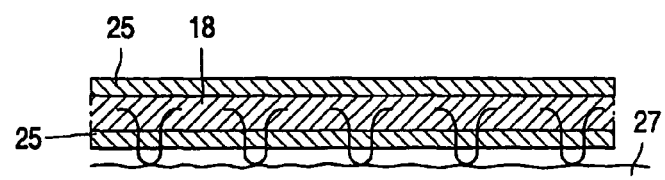

FIG. 3 presents a schematic view of an embodiment of the structure of the electrode when the electrode body is sandwiched between layers of an insulator.

Figure 4:
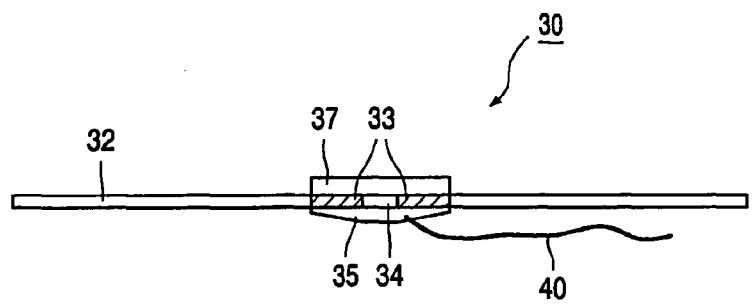

FIG. 4 presents a schematic view of an embodiment of the electrode being integrated in a wearable garment.

FIG. 1 presents a schematic view of the monitoring system 1. A patient 10 is supplied with a set of sensors 2, each sensor comprising an electrode according to the invention. The structure of the electrode will be discussed in more detail with reference to FIG. 2. The set of sensors 2 are positioned on the patient's skin in order to acquire a desirable physiological signal. For example, such a monitoring system can be arranged to perform measurements of the heart activity, respiration, blood pressure, myoactivity, EEG, etc. The sensors 2 comprising electrodes (not shown) are electrically connected to the storage and analysis device (SAD) 4. The SAD can be arranged to perform a primary data analysis in order to interpret the acquired physiological data, or it can serve as an intermediate data collection station. In the former case the control signal, for example an alarm can be sent to a remote station 6 upon an abnormality detection. In the latter case the data is being sent for analysis at the remote station. The latter case can be advantageous in situations where voluminous data is to be analyzed for different purposes.

Figure 2A:
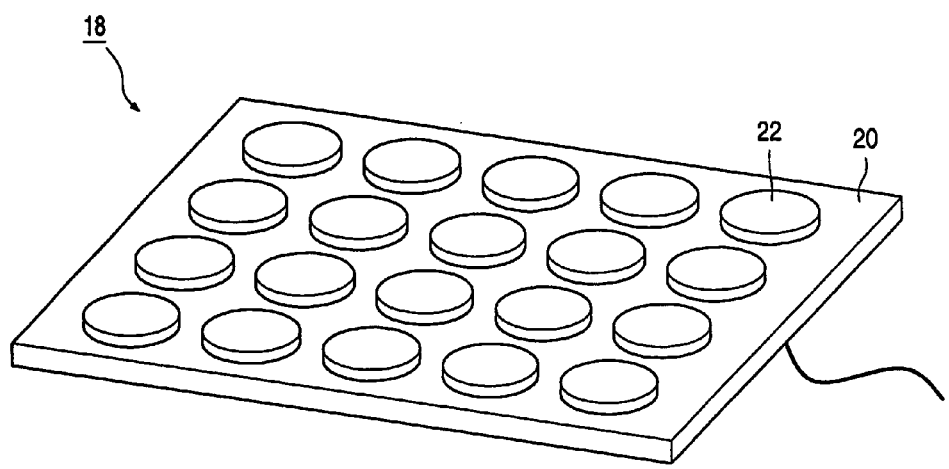
Figure 2B:
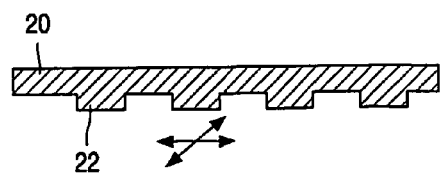

FIG. 2 presents a schematic view upon a working surface of the electrode to be used in the monitoring system according to the invention. In FIG. 2a it is shown that the electrode body 18 comprises a working surface 20 which is provided with a number of projections 22 to be put into contact with the patient's skin. Due to such an arrangement of the working surface 20 the actual surface area of the electrode which is brought into the contact with the patient is reduced, while being spatially distributed over a substantial total area. It is found that in such an arrangement a very low pressure is sufficient to keep the electrode in a constant contact with the patient's skin. Due to the fact that the electrode body 18 is manufactured from an elastic material, the projections 22 exhibit a certain degree of resiliency in two directions, which is schematically illustrated by arrows in FIG. 2b. This ensures that even in cases when the electrode body 18 exhibits minor translations with respect to the patient's skin, the tips of the projections 22 stay substantially at the same place, thus reducing the movement artifacts. In order to improve the electrical contact of the projections and the patient's skin, the projections can be provided with metal particles of can be fully coated with a metal layer. In this case the use of Ag is preferable as it is found that Ag enables a good skin contact. It must be noted that the optimal size of the projections depends on the particular application, reducing with an increase of the time the electrode has to be worn by the patient. Furtheron, it is also possible to provide holes in the electrode body 20 in the areas between the projections 22 in order to remove accumulated sweat from areas beneath the electrodes.

FIG. 3 presents a schematic view of the structure of the electrode when the electrode body 18 is sandwiched between layers of an insulator 25. The surface of the patient's skin is schematically given by a numerical 27. This configuration is found to be advantageous when the electrodes are to be worn durably. The insulator layer serves as a mechanical protection layer adding to the reliability of the monitoring system as a whole. The assembly, shown in FIG. 3 can be easily manufactured, namely by pressing a prefabricated projections (spheres, cylinders, cones) into a layer of a conductive elastic material. An example of such a material is a per se known conductive rubber. Then the resulting electrode body can be coated with plastic, so that only the tips of the projections protrude through the insulating layer 25. Also in this case it is possible to fabricate the projections with insertions of metal particles or coated with a metal layer. This technical measure is advantageous when the projections with a sub-mm size are utilized. All of the electrode structures discussed above have an advantage that they can easily be integrated in a wearable garment for continuous monitoring purposes. An example of such a garment is an elastic belt, which provides an additional surface tension on the electrodes further enabling better signal to noise ratio of the measurements.

FIG. 4 presents a schematic view of a garment-based monitoring system comprising an electrode 30 attached to the elastic belt 32. The working surface of the electrode 30 is given by a numerical 37. The elastic belt can also be integrated into a garment, for example an underwear slip or a brassier. The electrode material can be manufactured from a mixture of electrically conductive graphite with a silicon gel, for example. Other suitable materials can also be used to manufacture the electrode, for example conductive rubbers. Such an electrode can be integrated with the material of the belt by means of gluing, knitting or by means of applying a moulding operation. It is also possible that the elastic belt is pre-processed to comprise cut-aways in areas where the electrodes are to be positioned. As is shown in FIG. 4, a part of the electrode 34 is located in such a cut-away of the belt 32 and another part 33 of the electrode 30 is joined with the elastic belt 32. The outer body of the electrode 30 can be covered by the mould [not shown] at the backside surface 35 of the electrode 30. The electrical connections to the electrode 30 are realized by means of a wire, schematically presented by 40. This wire 40 leads to other electrodes in the monitoring system and to the motion sensor (optional) and to the Storage and Analysis Device (not shown) also attached to the belt. Thus, a cheap, durable and reliable wearable monitoring system can easily be realized using the method of the invention.

The invention claimed is:

1. An electrode for use in a monitoring system, the electrode comprising:
    a layer of electrically conductive elastic material;
    a plurality of submillimeter-sized prefabricated conductive metallic elements inserted in and projecting from a skin contacting face of the layer of electrically conductive elastic material, which metallic elements have surfaces configured to contact skin of a patient to be monitored; and
    an insulating plastic layer covering the skin contacting face of the electrically conductive elastic material with the surfaces of the conductive metallic elements projecting through the insulating plastic layer to contact the skin.

2. A monitoring system for monitoring a physiological activity of a recipient, comprising:
    a set of sensors including electrodes according to claim 1 to acquire physiological data;
    a device connected with the sensors to interpret the acquired physiological data.

3. The electrode according to claim 1, further including a plurality of ventilation holes extending through the electrically conductive elastic layer.

4. The electrode according to claim 1, wherein the layer of electrically conductive elastic material is mounted to an interior of a wearable garment.

5. The electrode according to claim 1, wherein the electrically conductive elastic material includes an electrically conductive rubber.

* * * * *